United States Patent [19]

Bombardieri

[11] Patent Number: 4,633,878
[45] Date of Patent: Jan. 6, 1987

[54] DEVICE FOR THE AUTOMATIC INSULIN OR GLUCOSE INFUSION IN DIABETIC SUBJECTS, BASED ON THE CONTINUOUS MONITORING OF THE PATIENT'S GLUCOSE, OBTAINED WITHOUT BLOOD WITHDRAWAL

[76] Inventor: Guiseppe Bombardieri, Via della Mendola, 47, Roma, Italy

[21] Appl. No.: 598,787

[22] Filed: Apr. 10, 1984

[30] Foreign Application Priority Data

Apr. 18, 1983 [IT] Italy ................. 48129 A/83

[51] Int. Cl.$^4$ ............................................. A61B 5/00
[52] U.S. Cl. ........................................ 128/635; 604/31
[58] Field of Search ............... 128/642, 639, 637, 635, 128/632; 604/31, 190, 240; 204/403, 415

[56] References Cited

U.S. PATENT DOCUMENTS

| | | | |
|---|---|---|---|
| 3,837,339 | 9/1974 | Aisenberg et al. | 604/50 |
| 3,983,864 | 10/1976 | Sielaff et al. | 436/68 |
| 4,265,249 | 5/1981 | Schindler et al. | 128/635 |
| 4,381,775 | 5/1983 | Nose et al. | 604/6 |
| 4,435,176 | 3/1984 | Ishikama | 604/190 |
| 4,436,094 | 3/1984 | Cerami | 128/635 |
| 4,447,191 | 5/1984 | Bilstad et al. | 604/122 |

OTHER PUBLICATIONS

"A Self-Calibrating, Continnous, In Vivo $pQ+pCO_2$ Monitor", Clark et al, 7-1977.
"Skeletal Muscle pQ; Indicator of Peripheral . . . Shock", Ninikoski et al, 1978.

Primary Examiner—Edward M. Coven
Attorney, Agent, or Firm—Bucknam and Archer

[57] ABSTRACT

A saline solution is pumped through a semi-permeable, hollow-fiber circuit implantable in a living body. A sensor determines the concentration of glucose in the solution. A microcomputer unit controls the supply of insulin and glucose to the body on the basis of the glucose concentration measurements. The hollow fibers form a filter through which only low molecular weight molecules may pass.

5 Claims, 1 Drawing Figure

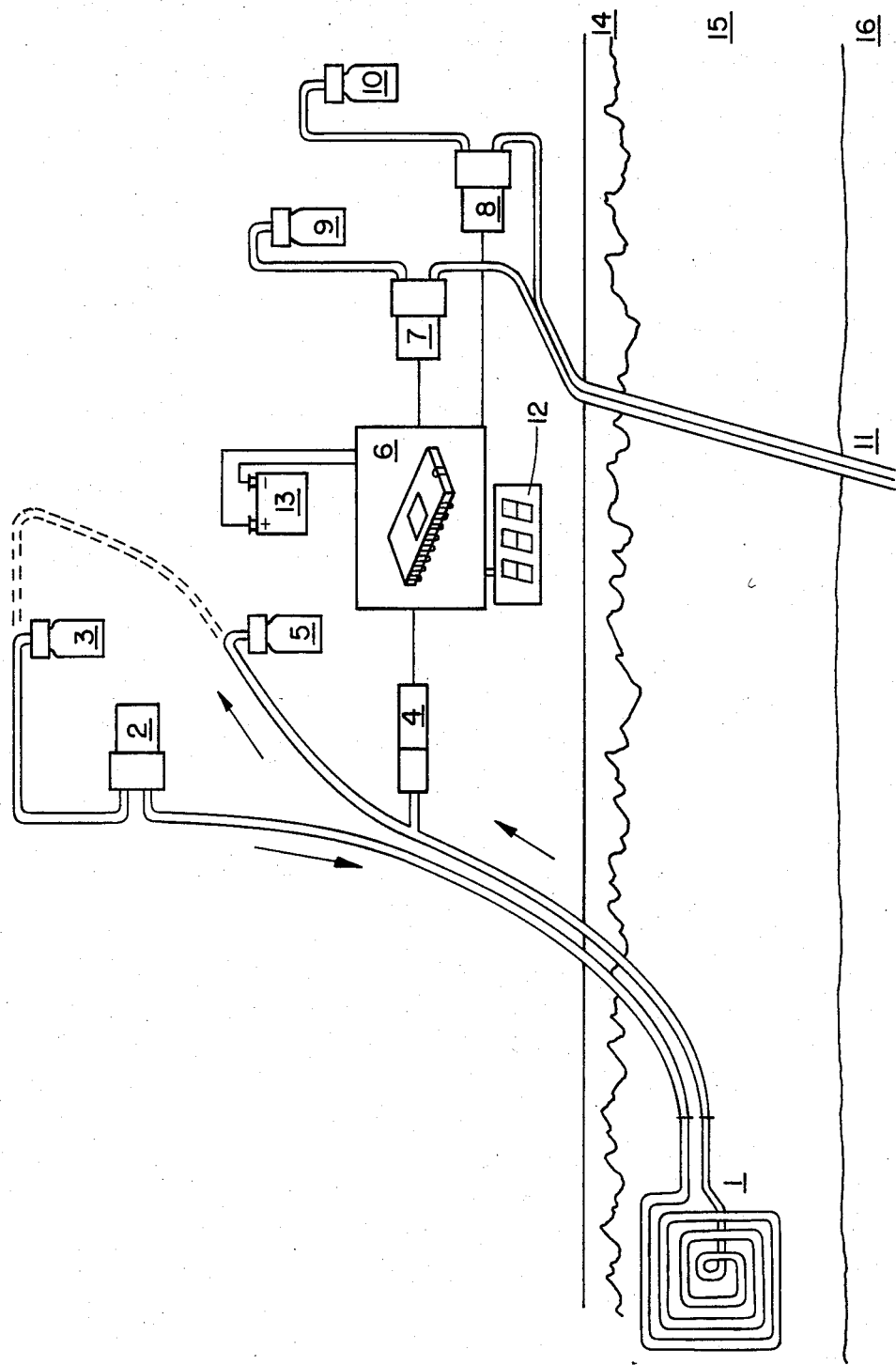

DEVICE FOR THE AUTOMATIC INSULIN OR GLUCOSE INFUSION IN DIABETIC SUBJECTS, BASED ON THE CONTINUOUS MONITORING OF THE PATIENT'S GLUCOSE, OBTAINED WITHOUT BLOOD WITHDRAWAL

BACKGROUND OF THE INVENTION

The present invention relates to feedback controlled or "closed-loop" insulin pumps known also as "artificial pancreases". These devices provide a continuous glucose determination in the diabetic patient. Data is transmitted from a glucose sensor to a microprocessor unit, which controls a pump for insulin, or glucose, infusion, in order to maintain blood glucose levels within a physiological range. Glucose determination in the known closed-loop insulin pumps is achieved by two different methods. In the first, blood is continuously withdrawn from a patient's vein and reaches a glucose sensor, directly or after ultrafiltration. The principal disadvantages of this system are blood loss and/or blood clotting in the drawing tubes. The second method for a continuous glucose assay consists of the insertion of the sensor into the patient's body, usually in the subcutaneous tissue, so that blood is not withdrawn. The drawback of this system is the rapid loss of sensor reliability, probably due to fibrin and some blood cells which unavoidably reach the sensor tip. The aforedescribed disadvantages of the known closed-loop insulin pumps permit only short-term use of the devices.

BRIEF SUMMARY OF THE INVENTION

In the system according to the present invention, the samples for a continuous glucose monitoring in the diabetic patient are obtained from a saline solution pumped through a hollow-fiber circuit, implanted in the patient's body. Hollow fibers are permeable to small molecules, or low molecular weight components. Thus, glucose diffuses into the fiber lumen from the surrounding body fluid. When equilibrium is reached, the pumped solution is ready for glucose assay by a suitable glucose sensor. This method avoids blood withdrawal, with the related clotting problems, and provides a long-term reliable glucose determination in diabetic patients. The present invention is of special interest for the realization of a "wearable" or implantable closed-loop insulin pump.

BRIEF DESCRIPTION OF THE DRAWINGS

In order that the invention may be readily carried into effect, it will now be described with reference to the single FIGURE, which is a block diagram of an embodiment of the device of the invention.

DETAILED DESCRIPTION OF PREFERRED EMBODIMENTS

The device of the invention consists of four principal components which are:
(a) the hollow-fiber saline solution circuit;
(b) the glucose sensor;
(c) the electronics;
(d) the infusion pumps.

(a) The Hollow-Fiber Saline Solution Circuit

This component is totally novel. A saline solution is pumped from a reservoir (3) to a glucose sensor (4) through a hollow-fiber circuit (1) by means of a piezoelectric or peristaltic pump (2). The hollow fibers are made of biocompatible material and are permeable only to small molecules or low molecular weight components. Plastic biocompatible material, such as polyacrylonitrile or polyethylene with a cut-off of 40,000, normally used in dialysis filters, may be used as the hollow fiber circuit material. Also suitable for such circuit are the materials marketed by Enka-Germany or Asahi Medical, Japan. The polyethylene may be obtained from Gambro, Sweden or Travenol, United States of America.

The hollow-fiber circuit must be implanted in the patient's body, usually in the subcutaneous tissue (15), through a short incision of the skin (14), using any local anaesthetic. The hollow fragility of the hollow fibers and the need of an adequate circuit length in a minimum space may require special arrangements of the fibers with suitable supports. The FIGURE shows a spiral-shaped hollow-fiber circuit (1), sustained by a small plastic disk (not shown in the FIGURE), implanted in the subcutaneous tissue of the abdominal wall (15). The hollow fiber number and length are chosen so as to obtain, in a short time, uniform concentration of glucose in the solution inside the fiber lumen and in the surrounding body fluid.

Biocompatible plastic tubes connect the implanted circuit with the pump (2) and with the glucose sensor (4). After the glucose assay, the solution flows towards a waste reservoir (5) or can be repumped to the hollow-fiber circuit via a circuit section indicated by broken lines in the FIGURE.

(B) The Glucose Sensor

The glucose sensor (4) is preferably an enzymatic-potentiometric one, commonly used in many laboratory instruments for blood glucose determination and also in the commercially-available "artificial pancreas", such as, for instance, the Biostator marketed by Miles Laboratories.

(c) The Electronics

The amplified signal coming from the glucose sensor (4) enters a microprocessor unit (6) by means of an analog to digital converter. The microprocessor (6) stores the data and, on the basis of a suitable algorithm (Albisser et al., *Diabetes,* May 1974), controls insulin and glucose infusion pumps (7) and (8), respectively. A display (12) of the microprocessor (6) indicates the data coming from the glucose sensor (4) and the amounts of the infused insulin and glucose. A suitable microprocessor (6) is that marketed by Motorola, Model MC1468705R3, a CMOS 8 byte MCU with timer, four-channel analog to digital converter, 2,8 Kbyte EPROM, 128 byte RAM, 4 I/O ports inside.

(d) The Infusion Pumps

An insulin pump (7) and a glucose pump (8) are controlled by the microprocessor (6). Solenoid or piezo-electric micropumps can be used to infuse insulin and glucose with high precision. Insulin and glucose are taken from special reservoirs (9 and 10), respectively, and can be infused into the patient by separate biocompatible catheters or by a single dual lumen catheter (11). The administration route can be the abdominal cavity (16), the subcutaneous tissue or a peripheral vein.

The power supply for the entire system is provided by a suitable battery or batteries (13).

The device according to the present invention has been tested in animals such as, for example, rabbits and guinea pigs, and humans ranging in age from 16 to 65 years old, for a period of at least two months without any loss of sensitivity because the hollow fibers filter does not become clogged up with blood or fibrin, so that the components of blood or fibrin do not reach the sensor tip. The glucose measurements made with the device according to the present invention have been compared with glucose measurements made with conventional laboratory apparatus, specifically a Yellows Springs YSI Model 23A instrument and the values agree, showing that the device of the invention provides reliable determinations. The coefficient of correlation is 0.98 between the apparatus of the present invention and the Yellow Springs apparatus. The device of the invention may be adapted to a size of $8 \times 10 \times 3$ cm and may be implanted into the abdominal wall of the patient. Thus, the present invention permits the avoidance of insertion of the sensor (4) directly into the subcutaneous tissue of a patient and, at the time, permits the avoidance of withdrawal of blood.

The device according to the present invention may be used not only in the case of diabetic patients for the determination of glucose, but also for the determination of many small molecular weight components in body fluids, such as sodium, potassium, calcium, and also medicines, for example, Digitalis, administered to humans in the body, so that their concentration may be monitored.

What is claimed is:

1. A device for the determination of the glucose content in the blood of a living body, which comprises a filter implantable in the subcutaneous tissue of said living body and composed of a circuit of biocompatible hollow fibers of polyacrylonitrile or polyethylene having a cut-off of 40,000 which are permeable to glucose but impermeable to the larger molecular weight components of the blood, means for circulating a saline solution through said filter located outside of the body whereby when said filter is implanted in said living body, glucose diffuses from the blood of said living body to said saline solution by dialysis and said saline solution after equilibrium is reached acquires the same concentration of glucose as in the blood of said living body; a sensor located outside of the body and in communication with said filter for determining the concentration of glucose connected to said filter.

2. The device according to claim 1 wherein said circuit is spiral shaped.

3. The device according to claim 1 wherein said filter is implantable in the abdominal wall of said living body.

4. The device as claimed in claim 1 further comprising control means connected to said sensor and linked to said living body for selectively introducing insulin or glucose to said living body to counteract glucose present in said solution in said filter in amounts above a determined range and to counteract an insufficiency of glucose in said filter in amounts below said determined range, respectively.

5. The device according to claim 4 wherein said control means comprises a source of insulin, an insulin pump connected to said source of insulin and linked to said living body, a source of glucose, a glucose pump connected to said source of glucose and linked to said living body and microprocessor means coupling said sensor to said insulin pump and to said glucose pump for operating said insulin pump to supply insulin to said living body when said sensor determines a glucose concentration greater than a determined level and for operating said glucose pump to supply glucose to said living body when said sensor determines a glucose concentration less than a determined level.

* * * * *